US00PP11793P2

(12) United States Plant Patent
VandenBerg

(10) Patent No.: US PP11,793 P2
(45) Date of Patent: Feb. 27, 2001

(54) CHRYSANTHEMUM PLANT NAMED 'CENTELLA'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/245,658

(22) Filed: Feb. 8, 1999

(51) Int. Cl.[7] ..... A01H 5/00
(52) U.S. Cl. ..... Plt./286

(58) Field of Search ..... Plt./286, 295, 296

*Primary Examiner*—Howard J. Locker
(74) *Attorney, Agent, or Firm*—C. A. Whealy

(57) ABSTRACT

A distinct cultivar of Chrysanthemum plant named 'Centella', characterized by its small, daisy-type inflorescences that are about 4 cm in diameter; attractive golden yellow ray florets; disc florets that when immature are dark red and when mature are dark yellow; numerous inflorescences per stem; large leaves; and good postproduction longevity with inflorescences maintaining good substance and color for about three weeks in an interior environment after one week of cool storage.

2 Drawing Sheets

BACKGROUND OF THE INVENTION

The present invention relates to a new and distinct cultivar of Chrysanthemum plant, botanically known as *Dendranthema grandiflora* and referred to by the cultivar name Centella.

The new Chrysanthemum is a product of a planned breeding program conducted by the Inventor in Salinas, Calif. The objective of the breeding program is to create new cut Chrysanthemum cultivars having inflorescences with desirable colors and good form and substance.

The new Chrysanthemum originated from a cross made by the Inventor in July, 1992, in Salinas, Calif., of a proprietary Chrysanthemum seedling selection identified as 2943 as the female, or seed, parent with a proprietary Chrysanthemum seedling selection identified as 2974, as the male, or pollen, parent.

The cultivar Centella was discovered and selected by the Inventor as a flowering plant within the progeny of the stated cross in a controlled environment in Alva, Fla., in November, 1993. The selection of this plant was based on its desirable inflorescence color and good form and substance.

Asexual reproduction of the new Chrysanthemum by terminal cuttings taken in a controlled environment in Alva, Fla., has shown that the unique features of this new Chrysanthemum are stable and reproduced true to type in successive generations.

SUMMARY OF THE INVENTION

The cultivar Centella has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Centella'. These characteristics in combination distinguish 'Centella' as a new and distinct cultivar:

1. Small, daisy-type inflorescences that are about 4 cm in diameter.

2. Attractive golden yellow ray florets.

3. Disc florets that when immature are dark red and when mature are dark yellow. Immature dark red disc florets give an "dark eye" appearance to the inflorescences.

4. Numerous inflorescences per stem.

5. Large leaves.

6. Good postproduction longevity with inflorescences maintaining good substance and color for about three weeks in an interior environment after one week of cool storage.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type.

The photograph at the top of the first sheet comprises a side perspective view of a typical flowering stem of 'Centella' grown as a spray-type cut Chrysanthemum.

The photograph at the bottom of the first sheet comprises a side perspective view of typical inflorescences of the cultivar Centella.

The photograph at the top of the second sheet comprises a top perspective view of upper (left) and lower (right) surfaces of typical inflorescences of the cultivar Centella.

The photograph at the bottom of the second sheet comprises a top perspective view of the upper (left) and lower (right) surfaces of leaves of the cultivar Centella. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Madrid, Cundinamarca, Colombia, under commercial practice in a single-layer polyethylene-covered greenhouse. Plants, grown as single-stem plants (not pinched), were planted on Apr. 29, 1998 and received 21 long day/short nights followed by short day/long nights until flowering. During the production time, the following environmental conditions were measured: day temperatures ranging from 24 to 38° C.; night temperatures ranging from 6 to 10° C.; and accumulated solar energy ranging from 16 to 27.6 KWH/$m^2$. Measurements and numerical values represent averages for six to ten typical flowering stems.

Botanical classification: *Dendranthema grandiflora* cultivar Centella.

Commercial classification: Daisy spray-type cut Chrysanthemum.

Parentage:

*Male or pollen parent.*—Unnamed proprietary *Dendranthema grandiflora* seedling selection, code number 2943.

*Female or seed parent.*—Unnamed proprietary *Dendranthema grandiflora* seedling selection, code number 2974.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy spray-type cut flower. Stems upright, uniform habit and freely branching.

*Flowering stem length.*—About 96.5 cm.

*Stem color.*—147B.

*Foliage description.*—Arrangement: Alternate. Length: About 10 cm. Width: About 8 cm. Apex: Acute to cuspidate. Base: Attenuate. Margin: Palmately lobed; sinuses, mostly parallel. Texture: Upper and lower surfaces slightly pubescent. Veins prominent on lower surface. Color: Young foliage upper surface: 147A. Young foliage lower surface: Between 147A and 147B. Mature foliage upper surface: 147A. Mature foliage lower surface: 147B. Venation upper surface: 147B. Venation lower surface: 147B. Petiole: Length: About 3 cm. Color: 147B.

Flowering description:

*Appearance.*—Daisy spray-type inflorescence form with oblong-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 56 days later.

*Postproduction longevity.*—In an interior environment, flowering stems will maintain good color and substance for about three weeks in an interior environment after one week of cool storage.

*Quantity of inflorescences.*—About 25 inflorescences per flowering stem.

*Inflorescence size.*—Diameter: About 4 cm. Depth (height): About 9 mm. Diameter of disc: About 1.4 cm.

*Ray florets.*—Shape: Oblong, fused at base. Length: About 2 cm. Width: About 8.5 mm. Apex: Rounded to slightly dentate. Base: Fused. Margin: Entire. Texture: Satiny, smooth, glabrous. Aspect: Upright to flat. Number of ray florets per inflorescence: About 23. Color: When opening: Upper surface: 9A with slight overtones of 34B. Lower surface: Close to 34B; base, 9A. Mature: Upper surface: 9A with slight overtones of 34B. Lower surface: 9A background with wide central stripe of close to 34B.

*Disc florets.*—Shape: Tubular. Length: About 6 mm. Width: Base, about 1 mm; apex, about 1.5 mm. Number of disc florets per inflorescence: About 180. Color: Immature: 154A to 59A. Mature: Apex: 12A. Mid-section: Light green. Base: White.

*Peduncle.*—Aspect: Strong and angled about 30° to the stem. Length: First peduncle: About 11.5 cm. Fourth peduncle: About 14 cm. Seventh peduncle: About 16 cm. Texture: Very fine pubescence. Color: Between 147A and 147B.

*Reproductive organs.*—Androecium: Present on disc florets only. Anther color: 12A. Amount of pollen: Moderate. Pollen color: 12A. Gynoecium: Present on both ray and disc florets.

Disease resistance: Resistance to diseases common to Chrysanthemums has not been observed on plants grown under commercial conditions.

Seed production: Seed production has not been observed.

It is claimed:

1. A new and distinct cultivar of Chrysanthemum plant named 'Centella', as illustrated and described.

* * * * *

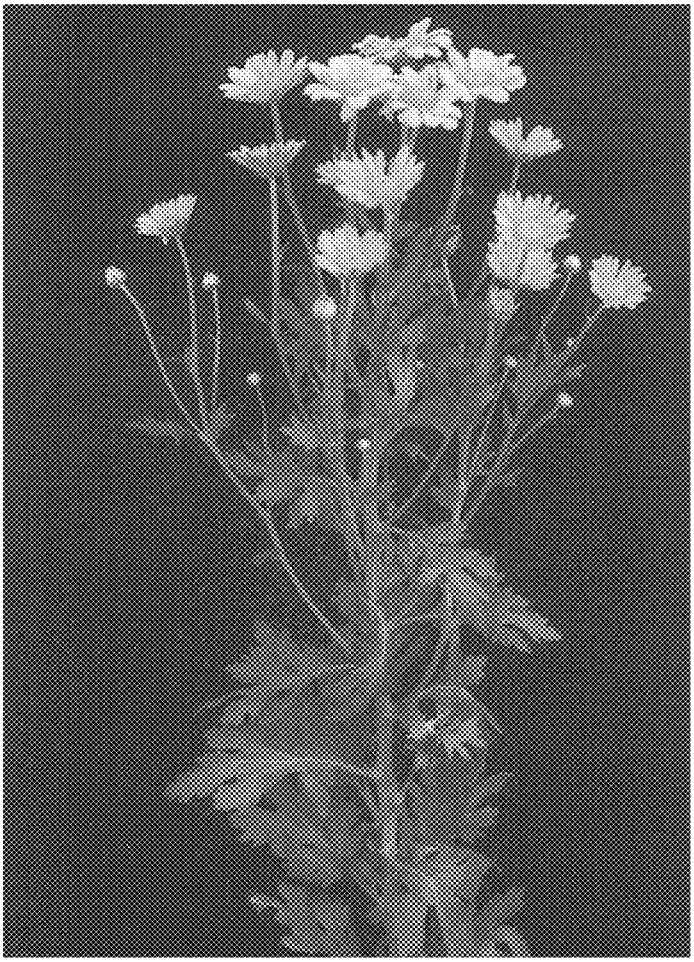
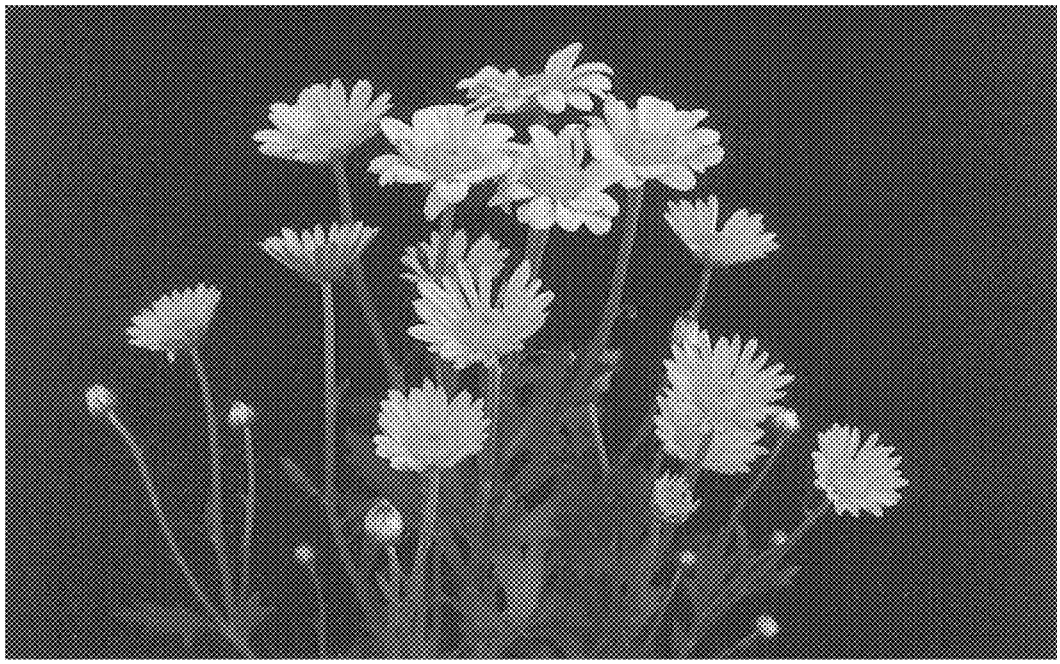

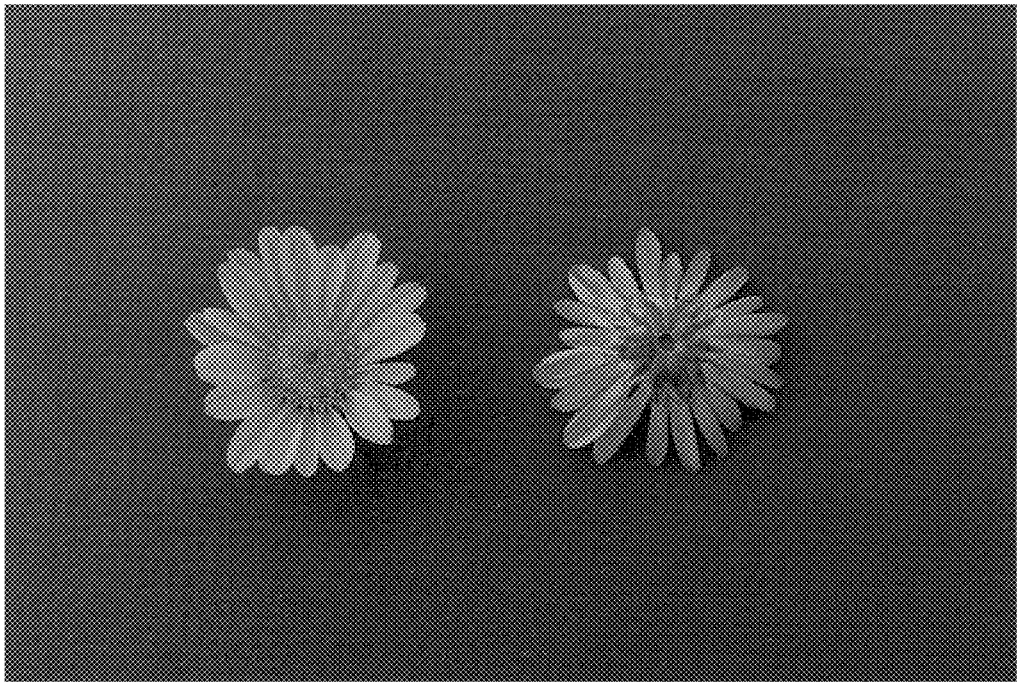
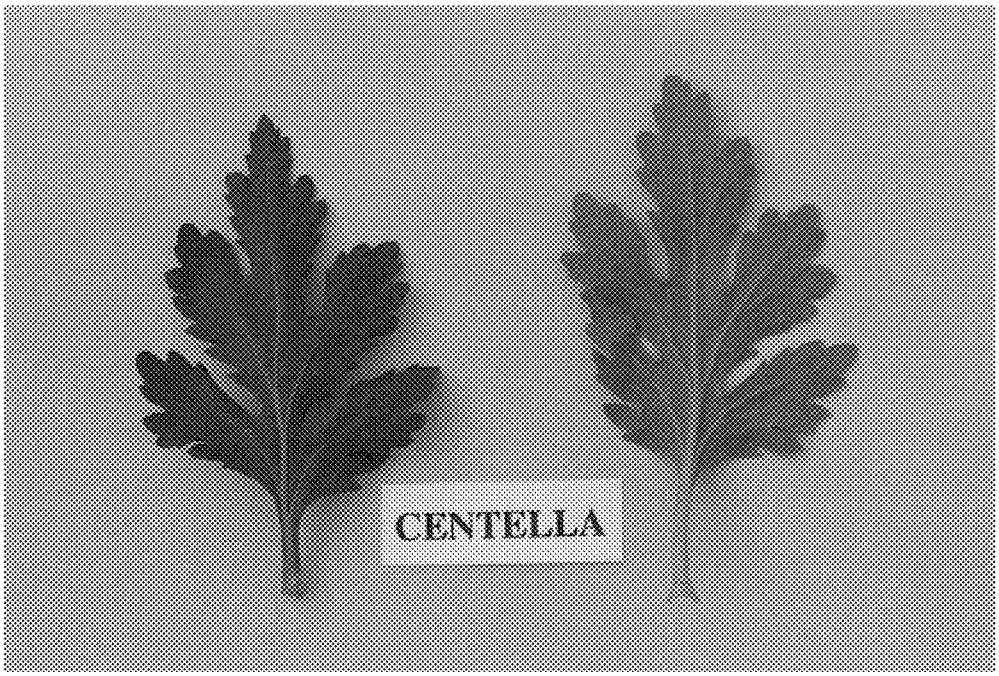
CENTELLA